United States Patent [19]

Arnold

[11] 4,113,751

[45] Sep. 12, 1978

[54] STABILIZER FOR ESTROGENS

[75] Inventor: Hanfried Arnold, Berlin, Fed. Rep. of Germany

[73] Assignee: Schering Aktiengesellschaft, Berlin and Bergkamen, Fed. Rep. of Germany

[21] Appl. No.: 751,676

[22] Filed: Dec. 17, 1976

Related U.S. Application Data

[63] Continuation-in-part of Ser. No. 731,436, Oct. 12, 1976, abandoned.

[30] Foreign Application Priority Data

Oct. 10, 1975 [DE] Fed. Rep. of Germany ....... 2546063

[51] Int. Cl.$^2$ ................................................ C07J 1/00
[52] U.S. Cl. ............................ 260/397.4; 260/397.45; 260/397.5

[58] Field of Search .......................... 260/397.4, 397.5

[56] References Cited

U.S. PATENT DOCUMENTS 3,649,621  3/1972  Stein et al. .................. 260/239.55 R

FOREIGN PATENT DOCUMENTS 590,113  7/1947  United Kingdom .................. 260/397.5

OTHER PUBLICATIONS

Chem. Abst., vol. 77, 1972, Par. 128,002 (J).
Chem. Abst., vol. 73, 1970, Par. 44,900(e).

*Primary Examiner*—Elbert L. Roberts
*Attorney, Agent, or Firm*—Millen & White

[57] ABSTRACT

Alkali metal salts of estrogen hemisulfates are stabilized with sodium acetate.

10 Claims, No Drawings

STABILIZER FOR ESTROGENS

CROSS-REFERENCE TO OTHER APPLICATIONS

This is a continuation-in-part of copending Application Ser. No. 731,436, filed Oct. 12, 1976 now abandoned.

BACKGROUND OF THE INVENTION

This invention relates to the stabilization, especially for the prevention of decomposition during long-term storage under dry conditions, of estrogens alkali metal sulfates.

Estrogen sulfates are contained in the urine of pregnant mares in the form of their water-soluble sodium salts. A mixture of these naturally occurring conjugated estrogens, consisting primarily of the sodium salts of the 3-hemisulfates of estrone, equilin, and equilenin, as well as the 17-dihydro derivatives thereof, viz., $17\alpha$-estradiol, $17\alpha$-equilol, and $17\alpha$-equilenol, is obtained by extraction and is utilized in therapy mainly for mitigating the complaints connected with the climacteric.

However, such mixtures do not always have the same composition and, therefore, they are standarized by the addition of synthetically prepared salts of other estrogen sulfates, e.g., estrone sulfate.

It is also possible to replace the mixture isolated from the urine completely by a synthetic mixture of sodium salts of the estrogen sulfates.

However, the alkali metal salts of these synthetic estrogen sulfates have the disadvantage that they are unstable in a pure, dry condition and decompose with the formation of the corresponding estrogen and alkali hydrogen sulfate.

A number of suggestions have been advanced to improve the stability of these compounds, for example by additions of the urine from mares (Canadian Pat. Nos. 691,988 and 922,627), of N-methylglucamine (U.S. Pat. No. 3,024,257), of other substituted amines (German Unexamined Laid-Open Application DOS No. 1,918,291), of amino acids (DOS No. 1,937,519), or by the preparation of the salts of quaternary ammonium bases (German Published Application DAS No. 1,032,740) in place of alkali metal salts of the estrogen sulfates.

However, these processes are technically complicated, utilize relatively expensive and/or nonphysiological additives, or lead to compounds which are soluble in water only with great difficulties.

It is an object of the present invention to provide a simple and physiologically acceptable stabilizer which is effective over an unlimited period of time.

SUMMARY OF THE INVENTION

In a composition aspect, this invention relates to mixtures, preferably pharmaceutically acceptable, of the alkali metal hemisulfate salt of one or more estrogens and an amount of sodium acetate effective to stabilize the alkali metal hemisulfate salt or salts under dry storage conditions.

In a process aspect, this invention relates to a process for stabilizing the alkali metal hemisulfate salt of one or more estrogens.

DETAILED DISCUSSION

The stabilizer is employed in the mixture in amounts of 0.5–50%, preferably 2–10% by weight, calculated on the estrogens salts. However, less than 0.5% has a measurable effect. Amounts larger than 50%, although not deleterious to the stabilizing effect, are unnecessary, since the desired activity is achieved with lesser amounts.

It is surprising that sodium acetate displays such a pronounced, stabilizing effect.

Any estrogen hemisulfate alkali metal salt which is unstable in storage can be stabilized with sodium acetate according to this invention. Natural or synthetic mixtures of two or more estrogen hemisulfate alkali metal esters can also be employed. As is well known, such estrogens possess an aromatic A-ring and a 3-hydroxy group and thus can form hemisulfate esters. Although the sodium salts of the estrogen hemisulfate esters and sodium acetate are preferred, other alkali metal salts, e.g., potassium salts, are contemplated equivalents.

It will be apparent to those skilled in the art that whereas pharmaceutically acceptable, i.e., injectable or ingestible, mixtures of the estrogen hemisulfate alkali metal salt and sodium acetate are preferred, stabilized mixtures which are to be stored prior to conversion to injectable or ingestable, unit dosage forms are also an aspect of this invention.

The pharmaceutical compositions of this invention like the unstabilized estrogens, can be administered subcutaneously, intramuscularly, or orally, the desired effects being manifested upon parenteral as well as oral administration. The daily dosage is determined by the activity and amount of estrogen present therein per unit dosage. The appropriate amounts are well known to the skilled in the art.

The pharmaceutical compositions of this invention are formulated in a conventional manner, e.g., by processing the stabilized estrogens or mixture of estrogens, together with carrier substances, diluents, flavor-ameliorating agents, etc., conventional in galenic pharmacy, into the desired form of administration, such as, for example, tablets, dragees, capsules, solutions, etc.

Particularly suitable for injections are oily solutions, such as, for example, solutions in sesame, castor or cottonseed oil. If desired, diluents or solubilizers can be added to increase the solubility, e.g., benzyl benzoate or benzyl alcohol. To achieve prolonged activity, the active agent can also be employed in microencapsulated form. Especially suitable for oral administration are capsules, tablets, dragees, pills, suspensions, emulsions, and solutions.

The preservative effect of the stabilizer utilized in accordance with this invention is evidenced, for example, by the fact that sodium estrone sulfate stored in a dry atmosphere at room temperature almost completely decomposes after three months, whereas sodium estrone sulfate admixed with 5% of sodium acetate, under the same storage conditions, showed no traces of decomposition.

The sodium acetate can be admixed with the estrogen, for example, by trituration and screening of the dry components, or by dissolution in a solvent, e.g., methanol, and evaporation of the solution to dryness, or by dissolving in water and they freeze-drying.

Without further elaboration, it is believed that one skilled in the art can, using the preceding description, utilize the present invention to its fullest extent. The following preferred specific embodiments are, therefore, to be construed as merely illustrative, and not limitative fo the remainder of the disclosure in any way whatsoever.

EXAMPLE 1

A mixture of estrogen sulfate sodium salts are stored in a dry atmosphere at room temperature of 23° C. plus 5% by weight of sodium acetate for up to 3 months. The results are give in the table below.

| Estrogen Sulfate Sodium Salt | 0 | 30 | 60 | 90 Days |
|---|---|---|---|---|
| Estrone | 99 | 99 (50) | 99 (20) | 99 (0) % |
| Equilin | 100 | 100 (95) | 100 (80) | 100 (50) |
| Equilenin | 100 | 100 | 100 | 100 |
| α-Estradiol | 100 | 100 | 100 | 100 |

The numerical values are the percentage of undecomposed estrogen sulfate sodium salt in the mixtures. The numerical values in parentheses give for comparison purposes, the percentage of undecomposed estrogen sulfate sodium salt stored in the absence of sodium acetate in a desiccator over potassium hydroxide.

EXAMPLE 2

Estrone sulfate sodium salt is stored at 60° C. with varying amounts of sodium acetate as the additive. The percentage of undecomposed salt is given in the table below.

| Sodium Acetate (%) | 0 | 30 Days |
|---|---|---|
| 0 | 98 | 0 |
| 0.5 | 98 | 5 |
| 2.0 | 98 | 98 |
| 5.0 | 98 | 98 |

The preceding examples can be repeated with similar success by substituting the generically and specifically described reactants and/or operating conditions of this invention for those ued in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A solid mixture of a storage unstable alkali metal salt of a 3-hemisulfate ester of a 3-hydroxy aromatic A-ring estrogen, and a stabilizing amount of sodium acetate.

2. A mixture according to claim 1 wherein the hemisulfate salt is the sodium salt and the mixture contains 0.5-50% by weight, calculated on the hemisulfate sodium salt, of sodium acetate.

3. A mixture according to claim 1 containing 2-10% by weight calculated on the hemisulfate alkali metal salt, of sodium acetate.

4. A mixture according to claim 3 wherein the estrogen is a mixture of naturally occurring conjugated estrogens.

5. A mixture according to claim 3 wherein the estrogen is estrone.

6. A mixture according to claim 3 where the estrogen is estradiol.

7. A method of stabilizing a storage unstable alkali metal salt of a 3-hemisulfate ester of a 3-hydroxy aromatic A-ring estrogen, which comprises storing said salt in admixture with a stabilizing amount of sodium acetate.

8. A method according to claim 7 wherein the estrogen hemisulfate alkali metal salt is the sodium salt and the stabilizing amount of sodium acetate is 0.5-50%, calculated on the estrogen hemisulfate sodium salt.

9. A method according to claim 8 wherein the stabilizing amount of sodium acetate is 2-10%, calculated on the estrogen hemisulfate sodium salt.

10. A method according to claim 9 wherein the estrogen is a mixture of naturally occurring conjugated estrogens.

* * * * *